(12) United States Patent
Takahashi (10) Patent No.: US 8,218,729 B2
(45) Date of Patent: Jul. 10, 2012

(54) CONTROL APPARATUS AND CONTROL METHOD

(75) Inventor: Naoto Takahashi, Kunitachi (JP)

(73) Assignee: Canon Kabushiki Kaisha, Tokyo (JP)

( * ) Notice: Subject to any disclaimer, the term of this patent is extended or adjusted under 35 U.S.C. 154(b) by 287 days.

(21) Appl. No.: 12/580,833

(22) Filed: Oct. 16, 2009

(65) Prior Publication Data

US 2010/0098215 A1 Apr. 22, 2010

(30) Foreign Application Priority Data

Oct. 17, 2008 (JP) .................................. 2008-268864

(51) Int. Cl.
*H05G 1/64* (2006.01)
(52) U.S. Cl. ...................................... 378/98.8; 378/147
(58) Field of Classification Search ................ 378/62, 378/98.8, 114, 116, 117, 145–147, 205
See application file for complete search history.

(56) References Cited

U.S. PATENT DOCUMENTS

| 6,222,906 B1 * | 4/2001 | Sakaguchi et al. ........... 378/98.8 |
| 2001/0033678 A1 | 10/2001 | Hirai |

FOREIGN PATENT DOCUMENTS

| CN | 1895173 A | 1/2007 |
| JP | 11-088688 A | 3/1999 |
| JP | 2000-070261 A | 3/2000 |
| JP | 2000-210273 A | 8/2000 |
| JP | 2001-351091 A | 12/2001 |
| JP | 2002-374418 A | 12/2002 |
| JP | 2003-076992 A | 3/2003 |

* cited by examiner

*Primary Examiner* — Courtney Thomas
(74) *Attorney, Agent, or Firm* — Canon U.S.A., Inc. IP Division (57) ABSTRACT

A control apparatus for controlling an X-ray irradiation area, in which an acquisition circuit acquires information relating to an effective area of a sensor, and a control circuit controls the X-ray irradiation area based on the information relating to the effective area.

10 Claims, 6 Drawing Sheets

601 SENSOR EFFECTIVE AREA

602 SET IRRADIATION AREA

FIG.6B

601 SENSOR EFFECTIVE AREA

603 ADJUSTED IRRADIATION AREA

CONTROL APPARATUS AND CONTROL METHOD

BACKGROUND OF THE INVENTION

1. Field of the Invention

The present invention relates to a control apparatus and a control method for controlling an X-ray irradiation area.

2. Description of the Related Art

Recently, in the field of X-ray imaging for medical use, with the progress of digital technology, digital X-ray imaging apparatuses using various methods have spread. An example of such an apparatus is a computed radiography (CR) apparatus, which forms a latent image of an X-ray intensity distribution on a photo-stimulable phosphor, excites the latent image by laser scanning this photo-stimulable phosphor, and reads the generated fluorescence by a photomultiplier tube.

Further, digital X-ray imaging apparatuses have been developed which directly digitize the X-ray image without going through an optical system, by using a flat panel detector (FPD). The FPD is an X-ray flat detection device in which a phosphor is closely attached to a large surface area amorphous silicon (a-Si) sensor. In addition, FPDs have also been developed which convert X-rays into electrons by direct photoelectric conversion using amorphous selenium (a-Se), gallium arsenide (GaAs), cadmium telluride (CdTe), lead iodide (PbI2), and mercury iodide (HgI2).

However, in a digital X-ray imaging apparatus which uses such an FPD, calibration typically is performed to correct the characteristics of the sensor due to unevenness in the sensitivity of each photoelectric conversion element and unevenness in the gain in the read circuit (hereinafter referred to as "gain correction").

The term calibration refers to the acquisition of correction data by irradiating the whole sensor surface roughly with uniform X-rays and performing imaging (this correction data is hereinafter referred to as "calibration data"). Further, the gain correction is performed by dividing (or logarithmically converting and then subtracting) the calibration data by the actually captured image of a subject (this image is hereinafter referred to as "captured image").

However, in the above calibration, when appropriate calibration data is not acquired, the gain correction may not be correctly performed. For example, when the X-ray irradiation area is limited during calibration to an area which is narrower than the whole sensor surface, at some of the calibration data areas, data which is roughly uniformly irradiated with X-rays cannot be obtained. Therefore, the gain correction cannot be correctly performed at some of the areas of the corresponding captured image. Further, when some kind of foreign substance is present between the X-ray tube and the sensor during calibration, a foreign substance shadow is included in the calibration data. Consequently, the gain correction similarly cannot be correctly performed at some of the areas of the captured image.

Various proposals have been made as a method for resolving such issues. For example, Japanese Patent Application Laid-Open No. 2000-070261 discusses a method which detects the X-ray irradiation area from the calibration data, and issues a warning when the whole sensor surface is not irradiated with the X-rays. In this method, the fact that the X-ray irradiation area is not appropriate can be clearly notified to an operator by issuing the warning, and an operator is prompted to acquire appropriate calibration data.

Japanese Patent Application Laid-Open No. 63-181742 discusses a method which detects the position of a head during calibration, and automatically retracts the head when the head is between the X-ray tube and the sensor. In this method, the inclusion of the shadow of the head, which is a foreign substance, in the calibration data can be avoided, and appropriate calibration data can be acquired.

Japanese Patent Application Laid-Open No. 2001-351091 discusses a method which performs capturing images a plurality of times during calibration, checks the dose, irradiation area, and whether a foreign substance is included from the plurality of acquired data, and notifies the operator of those results. In this method, the dose, irradiation area, and whether there is no inclusion of foreign substances can be clearly notified to the operator, and the operator can be prompted to acquire appropriate calibration data.

When performing the above calibration, there are cases where for some reason the whole sensor surface cannot be irradiated with the X-rays. For example, a sufficient distance may not be obtained between the X-ray tube and the sensor, or due to design restrictions, a foreign substance which is present between the X-ray tube and the sensor may shield the periphery of the sensor.

In such cases, it is difficult to acquire the appropriate calibration data. Consequently, the operator may start imaging as is even if there was a warning. Thus, when imaging the subject under these conditions, a non-effective area is present where gain correction is not correctly performed at some areas of the captured image. However, in the conventional methods, there is no method which allows the operator to confirm beforehand such a non-effective area in the captured image. Therefore, imaging may be performed while the operator does not realize that the area of interest used for diagnosis is included in this non-effective area. Further, from the standpoint of protecting the subject from exposure, imaging the subject by irradiating the whole sensor surface with X-rays although the non-effective area is present, may be an issue.

SUMMARY OF THE INVENTION

According to an aspect of the present invention, a control apparatus includes an acquisition unit configured to acquire information relating to an effective area of a sensor, and a control unit configured to control an X-ray irradiation area based on the acquired information.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
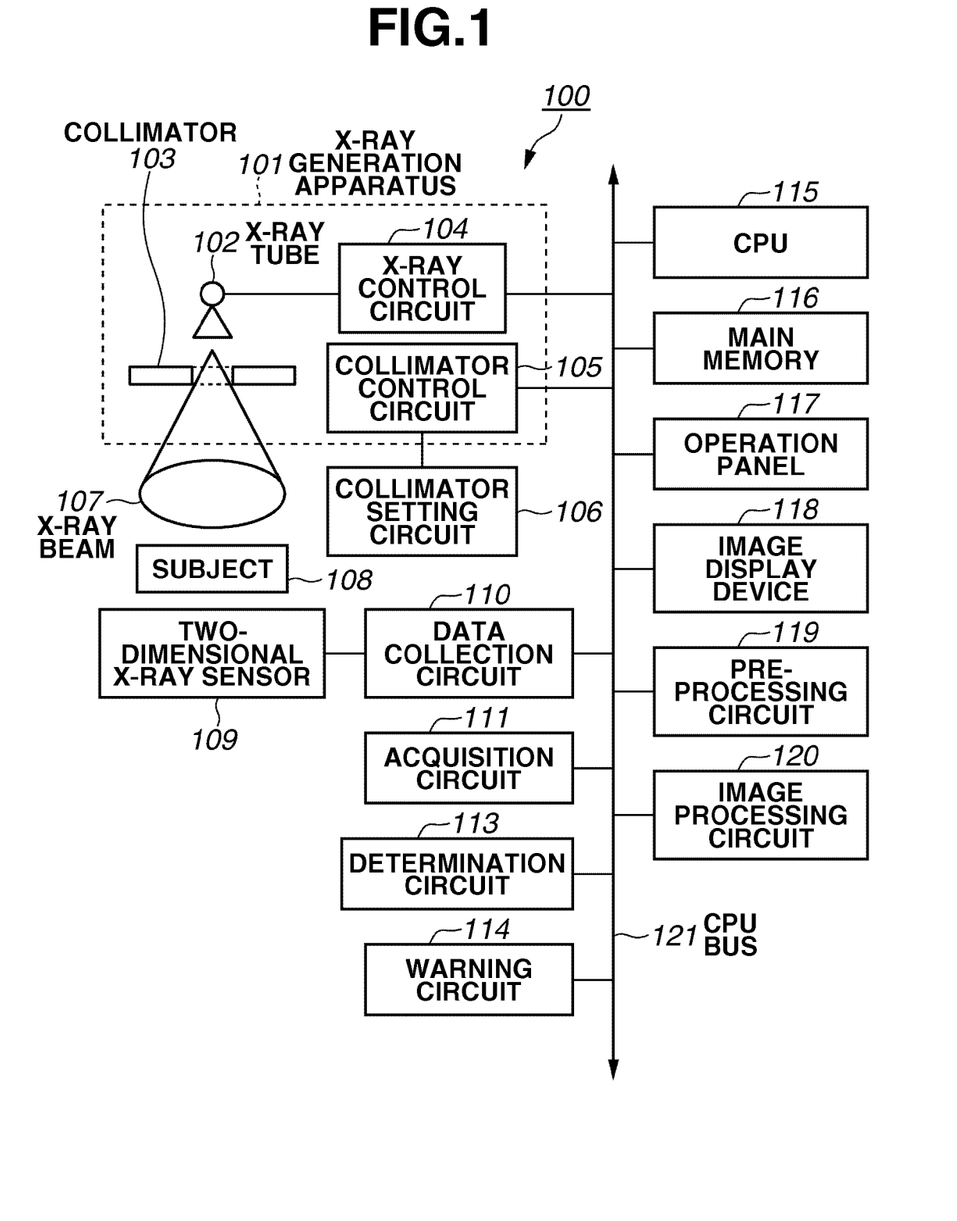
FIG. 1 is a configuration diagram of an entire X-ray imaging apparatus according to an exemplary embodiment of the present invention.

FIG. 1 illustrates an entire X-ray imaging apparatus according to an exemplary embodiment of the present invention.

The present invention is applied to an X-ray imaging apparatus 100 like that illustrated in FIG. 1, for example. The X-ray imaging apparatus 100 has a function for outputting a captured image acquired by exposing a subject to X-rays on a film or an image display device 118. An X-ray generation apparatus 101 (e.g. X-ray generation circuit) includes an X-ray tube 102 which apply an X-ray beam 107 on a light receiving surface of a two-dimensional X-ray sensor 109 under the control of an X-ray control circuit 104. The X-ray generation apparatus 101 also includes a collimator 103 for controlling the X-ray irradiation area irradiated by the X-ray tube 102. The position of the collimator 103 is controlled by a control circuit 105 (i.e., collimator control circuit). The X-ray imaging apparatus 100 also includes a collimator operation unit 106 (e.g., collimator setting circuit) for inputting information relating to the position of the collimator into the control circuit 105. The collimator operation unit 106 has an operation unit such as a dial or operating lever (not illustrated).

The two-dimensional X-ray sensor 109 acquires an analog image signal by performing a photoelectric conversion based on a two-dimensional intensity distribution of the X-rays irradiated from the X-ray generation apparatus 101.

A data collection circuit 110 converts the analog image signal acquired by the two-dimensional X-ray sensor 109 into a digital image signal (also called "image data"), and supplies the digital image signal to each circuit under control of a central processing unit (CPU) 115 via a CPU bus 121.

An acquisition circuit 111 acquires an effective area of the sensor from information relating to the X-ray irradiation area during calibration.

A determination circuit 113 determines whether the collimator position is appropriate based on the position of the collimator 103 and the effective area. A warning circuit 114 issues a warning when it is determined by the determination circuit 113 that the collimator position is not appropriate.

The CPU 115 controls the whole operations of the X-ray imaging apparatus 100 based on operations in an operation panel 117 according to a program stored in a main memory 116.

The X-ray imaging apparatus 100 also includes the image display device 118, a pre-processing circuit 119, and an image processing circuit 120. These units are connected to each other via the CPU bus 121 so that they are capable of transferring data.

In such an X-ray imaging apparatus 100, the main memory 116 stores the various kinds of data which are used for the processing by the CPU 115. In addition, the main memory 116 functions as a working memory of the CPU 115. The CPU 115 controls the operations of the whole apparatus based on operations in the operation panel 117 using the main memory 116.

The X-ray control circuit 104 controls the X-rays irradiated from the X-ray tube 102 by adjusting tube current, tube voltage, and irradiation time. The control circuit 105 controls the X-ray irradiation area by adjusting a diaphragm amount of the collimator 103. The control circuit 105 also has a CPU 130 (not illustrated) and operates based on a program stored in a memory 140 (not illustrated). The memory 140 stores the various kinds of data used for the processing by the CPU 130. In addition, the memory 140 functions as a working memory of the CPU 130. By using the memory 140, the CPU 130 controls the operations of the collimator 103, acquisition circuit 111, determination circuit 113, and warning circuit 114 based on operations in the collimator operation unit 106. A CPU 115 can also control operations by receiving control from a synergistic processing unit (SPU).

The two-dimensional X-ray sensor 109 acquires the analog image signal by performing a photoelectric conversion based on the two-dimensional intensity distribution of X-rays irradiated from the X-ray generation apparatus 101. The data collection circuit 110 converts the analog image signal acquired by the two-dimensional X-ray sensor 109 into a digital image signal, and supplies the digital image signal to each circuit under control of the CPU 115 via the CPU bus 121.

Figure 2:
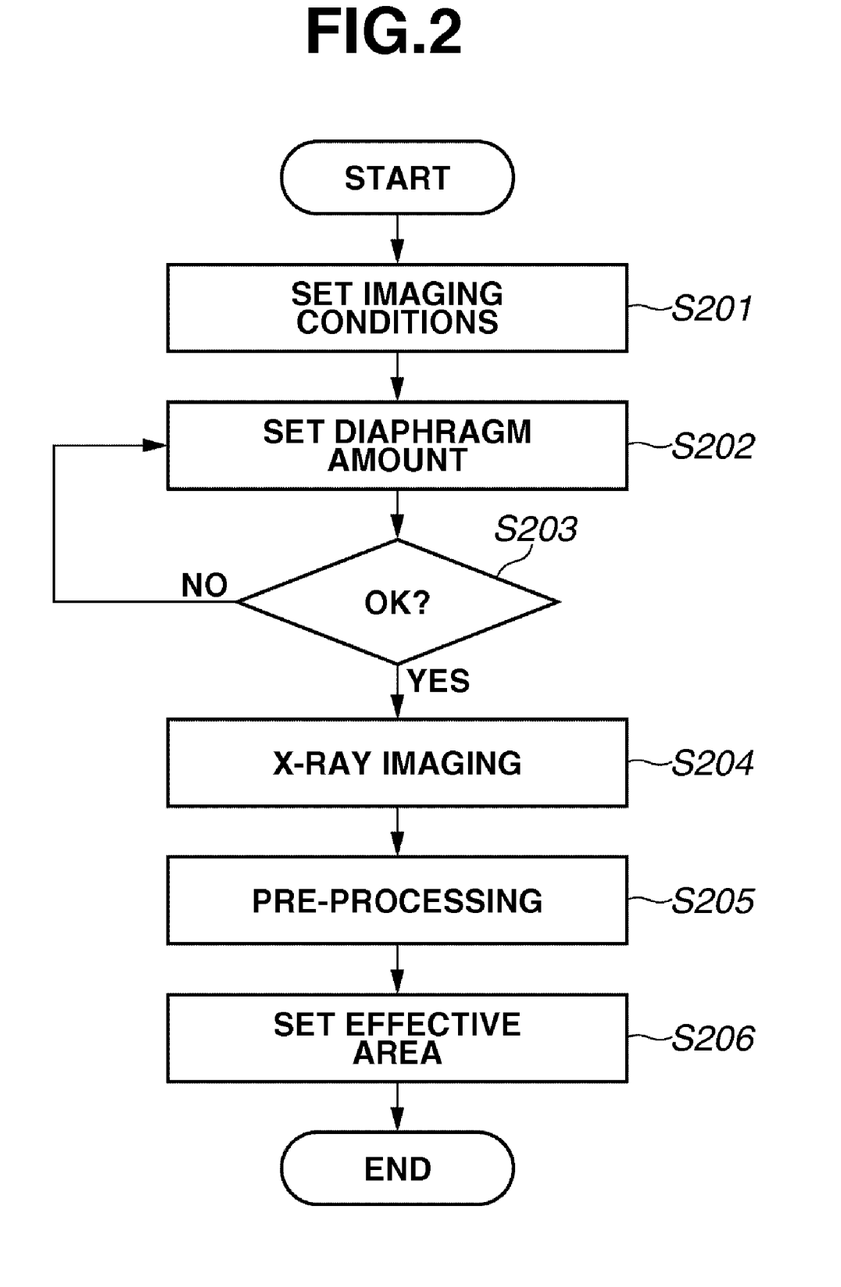
FIG. 2 is a flowchart illustrating a processing order of a calibration operation according to an exemplary embodiment of the present invention.

FIG. 2 is a flowchart illustrating a calibration flow according to an exemplary embodiment of the present invention.

Figure 3:
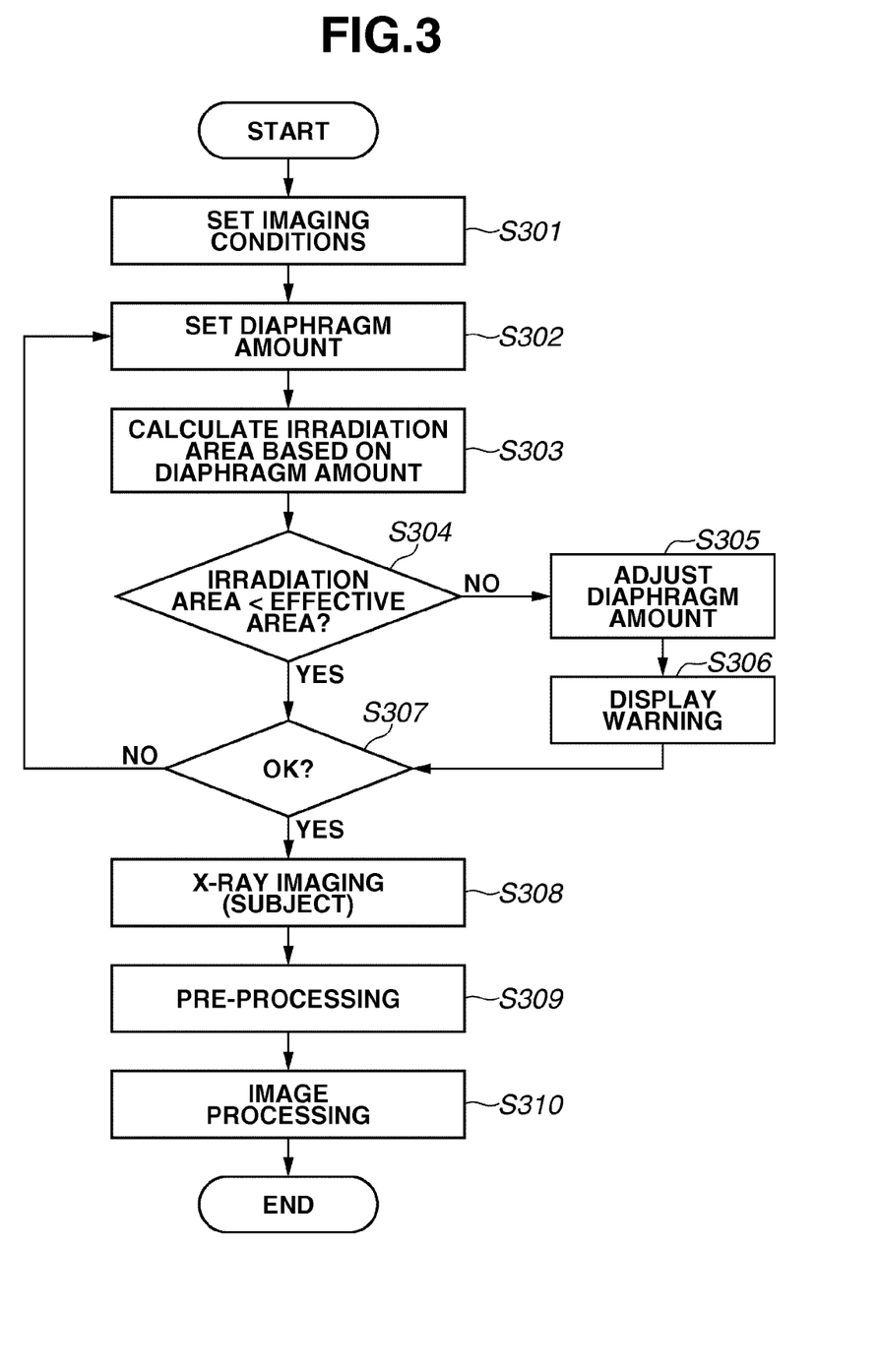
FIG. 3 is a flowchart illustrating a processing order of an imaging operation according to an exemplary embodiment of the present invention.

FIG. 3 is a flowchart illustrating an imaging operation flow according to an exemplary embodiment of the present invention.

The operations in the calibration and imaging according to the present exemplary embodiment having the above-described configuration will now be described in more detail using the flowcharts of FIGS. 2 and 3.

The operations in the calibration of the X-ray imaging apparatus 100 illustrated in FIG. 1 will be described using FIG. 2. First, in step S201, the operator (X-ray technician etc.) sets the imaging conditions, such as imaging distance, tube voltage, tube current, and irradiation time, via the operation panel 117.

Next, in step S202, the operator sets the diaphragm amount via the collimator operation unit 106. At this point, selection can be made between a first mode in which a brake is applied and a second mode in which a brake is not applied on the operations by the collimator operation unit 106.

When the first mode is selected, the brake is applied on the operations of the collimator operation unit 106 based on a signal output from the control circuit 105. On the other hand, when the second mode is selected, a brake is not applied on the operations of the collimator operation unit 106. Whether the first mode or the second mode is selected is determined by the control circuit 105.

During calibration, the non-brake-applying second mode is selected.

The set diaphragm amount is sent to the control circuit 105. The control circuit 105 operates the collimator 103 based on the set diaphragm amount. The collimator 103 has a rectangular shape, in which the respective open/closed amounts can be set in the vertical and horizontal directions by the collimator operation unit 106. The area where the X-rays are irradiated on the two-dimensional X-ray sensor 109 can be confirmed using visible light (not illustrated) from a lamp or the like.

In step S203, the operator confirms the X-ray irradiation area with visible light irradiated on the two-dimensional X-ray sensor 109. If the X-ray irradiation area is not appropriate (NO in step S203), the processing returns to step S202, and the diaphragm amount is readjusted. While in the calibration the diaphragm amount is adjusted so that the X-rays are irradiated on the whole surface of the two-dimensional X-ray sensor 109, if for some reason the X-rays cannot be irradiated on the whole surface, the diaphragm amount is adjusted so that the X-rays are irradiated over as wide an area as possible.

Next, in step S204, X-ray imaging is started in a state where a subject 108 is not present by pressing an exposure button (not illustrated). In the X-ray imaging, the X-ray control circuit 104 controls the X-ray tube 102 to irradiate with the X-ray beam 107. The irradiated X-ray beam 107 reaches the two-dimensional X-ray sensor 109, where it is converted into a digital image signal by the data collection circuit 110. This digital image signal is then supplied to the pre-processing circuit 119. The control circuit 105 sends the collimator position and the irradiation area to the data collection circuit 110 when the exposure button (not illustrated) is pressed.

In step S205, the pre-processing circuit 119 performs offset correction and defect correction on the digital image signal supplied from the data collection circuit 110. This digital image signal which was subjected to pre-processing by the pre-processing circuit 119 is stored in the main memory 116 as image data for calibration. Further, a reduced image or image data on which correction processing was not performed may also be stored in the main memory 116 as image data for calibration.

Although according to the present exemplary embodiment, the calibration data is acquired in one imaging, the present exemplary embodiment is not limited to this. For example, a plurality of calibration data may also be acquired by repeating the operations of steps S204 and S205 a plurality of times. Further, one piece of calibration data may be stored in the main memory 116 by averaging the plurality of calibration data.

Figure 4:
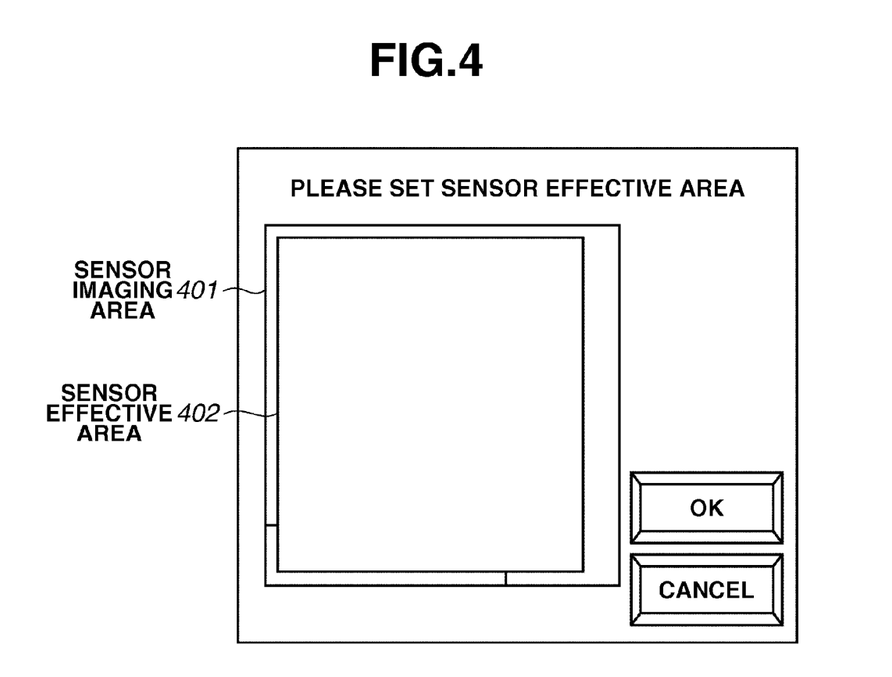
FIG. 4 illustrates a method for setting an effective area of a sensor according to an exemplary embodiment of the present invention.

Next, in step S206 (set effective area), the area where the X-rays were roughly uniformly irradiated is acquired as the effective area by the acquisition circuit 111, and the effective area information is stored in the main memory 116. The method for setting the effective area is not especially limited. For example, as illustrated in FIG. 4, the effective area may be set by displaying the calibration data on the image display device 118 and allowing the operator to set an effective area 402 on the two-dimensional X-ray sensor illustrated by a solid line with a touch panel or a mouse from among a sensor imaging area 401 illustrated by a solid line. Further, in step S206, as described above, the position of the collimator 103 when the exposure button (not illustrated) was pressed may be stored in the main memory 116 as information about the effective area.

The irradiated area may also be automatically recognized. An example of a method for automatically recognizing the irradiated area is to extract the area in which the X-rays are being directly irradiated on the light receiving surface of the two-dimensional X-ray sensor, as the irradiation area by image processing. In this case, the area in which the X-rays are being directly irradiated on the light receiving surface of the two-dimensional X-ray sensor may be set as the effective area of the two-dimensional X-ray sensor. Such an image processing method is known in the art, and thus a detailed description thereof is omitted here. For example, the irradiation area can be automatically recognized by awarding points for field edge similarity based on a pattern of a pixel of interest and the pixel values of the pixels surrounding that pixel.

The image to be used can be a reduced image stored in the main memory 116 or image data on which correction processing was not performed.

The imaging operations in the X-ray imaging apparatus 100 illustrated in FIG. 1 will now be described using FIG. 3. First, in step S301, the operator positions the subject 108 at an appropriate position relative to the two-dimensional X-ray sensor 109 and sets the imaging conditions, such as imaging distance, tube voltage, tube current, and irradiation time, via the operation panel 117.

In step S302, if the non-brake-applying second mode is selected, the operator sets the diaphragm amount via the collimator operation unit 106 based on a type of the subject body and a test. The set diaphragm amount is sent to the control circuit 105. Further, the control circuit 105 operates the collimator 103 based on the set diaphragm amount, and stores the diaphragm amount in the main memory 116. The collimator 103 has a rectangular shape, in which the respective open/closed amounts can be set in the vertical and horizontal directions by the collimator operation unit 106.

Figure 5:
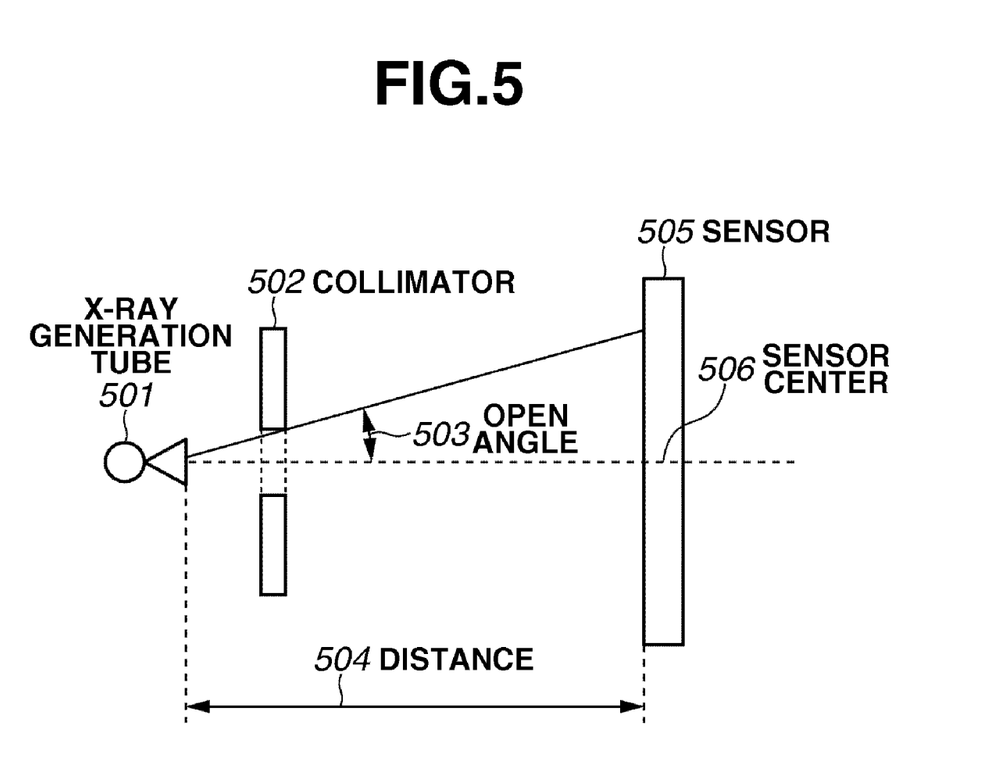
FIG. 5 illustrates a method for calculating an X-ray irradiation area according to an exemplary embodiment of the present invention.

Next, the control circuit 105 reads from the main memory 116 the set diaphragm amount of collimator operation unit 106 and the information about the effective area set during calibration, and determines whether the X-ray irradiation area is not larger than the effective area. First, in step S303 (calculate irradiation area based on diaphragm amount), the X-ray irradiation area in the image acquired by the two-dimensional X-ray sensor 109 is calculated from the diaphragm amount of the collimator operation unit 106. As a method for calculating the irradiation area from the diaphragm amount, a method described in Japanese Patent Application Laid-Open No. 2000-210273 may be used. For example, when calculating the irradiation area in the upward direction, as illustrated in FIG. 5, if a distance 504 from an X-ray tube 501 to a sensor 505 is d (cm), and an open angle 503 in the upward direction is a, the irradiation area in the upward direction can be calculated by the following equation (1) as an offset amount (Au) (pixel) from a sensor center 506 of the sensor 505. The irradiation areas in the downward and left/right directions may be calculated in a similar manner.

$$Au = d \times \tan(a)/p \tag{1}$$

Here, p is the image size (cm) of the sensor. Obviously, the effective area can also be determined from the position of the collimator 103 stored during calibration.

Figure 6A:
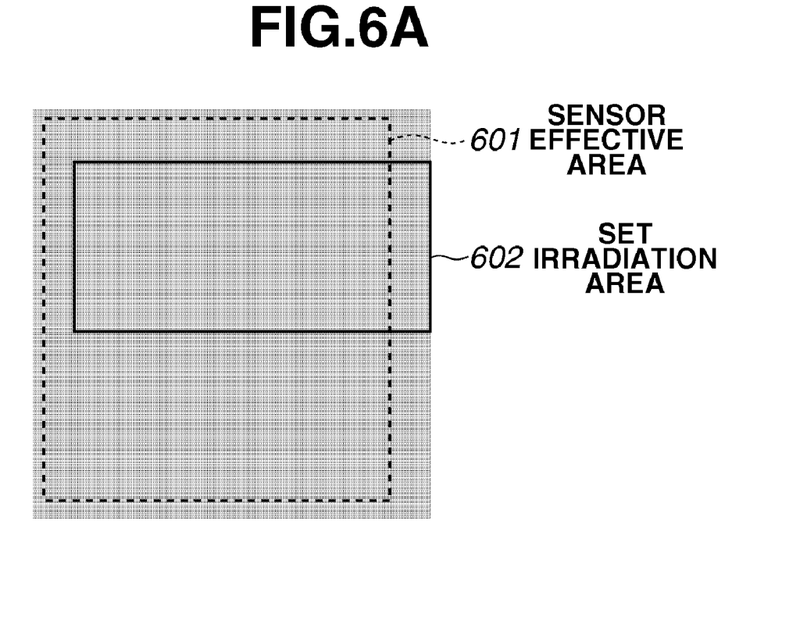
FIGS. 6A and 6B illustrate a method for correcting an X-ray irradiation area according to an exemplary embodiment of the present invention.
Figure 6B:
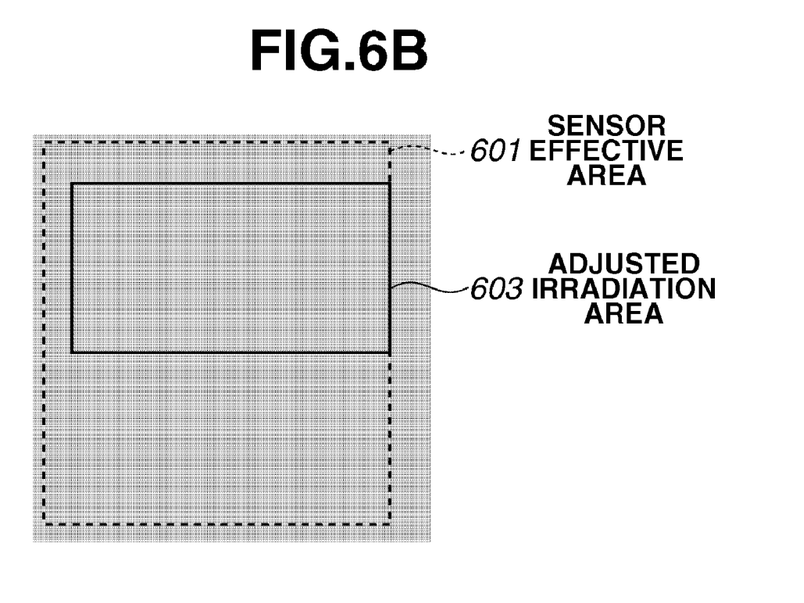

Next, in step S304, the size of the irradiation area and the effective area are compared. If the irradiation is smaller than the effective area, then the process goes to step 307. Otherwise, the process proceeds to step S305. For example, when at least one side of an irradiation area 602 in FIG. 6A indicated by a solid line is set (set irradiation area 602) to be wider than a sensor effective area 601 indicated by a dotted line (the right direction in FIG. 6A), in step S305, the diaphragm amount is adjusted like in FIG. 6B so that the irradiation area (adjusted irradiation area 603) is not wider than the sensor effective area 601. Further, in step S306 (display warning), a warning that the irradiation area was set to be wider than the effective area is sent to the operator by the warning circuit 114.

When the first mode is selected, a brake is applied on the operations of the collimator operation unit 106 by an output signal of the control circuit 105. For example, when the operations of the collimator operation unit 106 are performed via a mechanical operation such as the one performed with a dial or a switch, a mechanical brake is applied with information relating to the effective area as a reference. The brake is applied by the control circuit 105 so that the force used for operation increases as the X-rays which should be output from the collimator approach the effective area. Further, when the operations of the collimator operation unit 106 are not made via a mechanical operation, but are made via an input operation using a touch panel or the like, the range of the movement amount of the collimator is changed based on the amount of the input operation with the effective area as a reference. The brake is applied by the control circuit 105 so that the movement amount with respect to the operation decreases as the X-rays which should be output from the collimator approach the effective area.

When the second mode is selected, in step S307, the operator can also confirm the X-ray irradiation area by visible light irradiated on the two-dimensional X-ray sensor 109. If the X-ray irradiation area is not appropriate (NO in step S307), the processing returns to step S302, and the diaphragm amount is readjusted. In such a case, a brake from the control circuit 105 is not applied via the collimator operation unit 106.

After the diaphragm adjustment is finished, in step S308, the operator presses an exposure button (not illustrated) to start X-ray imaging. In the X-ray imaging, the X-ray control circuit 104 controls the X-ray tube 102 to irradiate with the X-ray beam 107. The irradiated X-ray beam 107 is transmitted attenuating through the subject 108, and reaches the two-dimensional X-ray sensor 109, where it is converted into a digital image signal by the data collection circuit 110. This digital image signal is then supplied to the pre-processing circuit 119.

In step S309, the pre-processing circuit 119 performs offset correction and defect correction on the digital image signal supplied from the data collection circuit 110. Further, in step S309, the pre-processing circuit 119 reads the calibration data from the main memory 116, and performs gain correction. The gain correction can be performed by dividing (or logarithmically converting and then subtracting) the calibration data by the acquired digital image signal. This digital image signal which was subjected to pre-processing by the pre-processing circuit 119 is stored in the main memory 116 as the captured image, and supplied to the image processing circuit 120.

In step S310, processing for converting the captured image into an image suitable for diagnosis is performed by the image processing circuit 120. For example, processing such as increasing sharpness, dynamic range compression, noise reduction, and gradation conversion is performed. The method for each processing item is not especially limited. For example, already known methods may be used, such as the one using an unsharp mask image (Japanese Patent Application Laid-Open No. 2002-374418), producing an image with a plurality of frequency components by wavelet conversion or Laplacian pyramid decomposition, and then performing processing (Japanese Patent Application Laid-Open No. 2003-076992), and gradation conversion by an S-shaped curve (Japanese Patent Application Laid-Open No. 11-088688). Not all of these processing items have to be performed. For example, only the processing set by the operation panel 117 may be selectively performed.

In the present exemplary embodiment, the operator can clearly confirm a non-effective area from a warning which is displayed when the collimator is set for a non-effective area of the sensor. In the non-effective area, gain correction is not correctly performed before imaging. Further, the subject can be thoroughly protected from exposure by automatically limiting the collimator so that X-rays are not irradiated on such a non-effective area.

As described above, the X-ray irradiation area can be controlled even when the X-rays are not irradiated on the entire light receiving surface of the sensor during calibration.

The present invention may also use a recording medium on which a software program code for realizing the functions of the above exemplary embodiment is recorded. More specifically, the present invention is also achieved by supplying a recording medium to a system or an apparatus, and having a computer (or a CPU or a micro processing unit (MPU)) of the system or apparatus read and execute the program code stored in the recording medium. In this case, the program code itself read from the recording medium realizes the functions of the above exemplary embodiment, so that the recording medium on which the program code is recorded constitutes the present invention.

Examples of storage media which can be used for supplying the program code include a flexible disk, a hard disk, an optical disk, a magneto-optical disk, a compact disc read only memory (CD-ROM), a CD-R, a magnetic tape, a nonvolatile memory card, a ROM and the like.

Further, the present invention also includes embodiments where, based on an instruction from the program code, an operating system (OS) or the like running on the computer performs part or all of the actual processing, and by that processing the functions of the above-described exemplary embodiment are realized.

Further, the present invention also includes cases where the program code read from the recording medium is written into a memory provided on a function expansion board inserted into the computer or a function expansion unit connected to the computer. In such a case, based on an instruction from the program code, a CPU or the like provided on the function expansion board or function expansion unit performs part or all of the actual processing, and by that processing the functions of the above-described exemplary embodiment are realized.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-268864 filed Oct. 17, 2008, which is hereby incorporated by reference herein in its entirety.

What is claimed is:

1. An apparatus for controlling an X-ray irradiation area generated by an X-ray generation apparatus, comprising:
    an acquisition unit configured to acquire information relating to an effective area of a sensor, wherein the effective area is acquired based on an irradiation area of X-rays during calibration;
    a collimator configured to limit the irradiation area of X-rays; and
    a control unit configured to limit a movement range of the collimator based on the effective area.

2. The apparatus according to claim 1, wherein the acquired information is based on a distance between the X-ray irradiation area in an image acquired from a sensor and an X-ray tube irradiating the sensor with the X-rays.

3. The apparatus according to claim 1,
    wherein the effective area is acquired based on a position of the collimator during calibration.

4. The apparatus according to claim 3, further comprising:
    a determination unit configured to determine whether the position of the collimator is appropriate based on information relating to the position of the collimator and the effective area; and
    a warning unit configured to issue a warning when the determination unit determines that the position of the collimator is not appropriate.

5. The apparatus according to claim 3, further comprising a determination unit configured to determine whether the position of the collimator is appropriate based on information relating to the position of the collimator and the effective area, wherein the control unit is configured to limit the movement range of the collimator based on the determination of the determination unit.

6. The apparatus according to claim 3, further comprising a collimator operation unit configured to input information relating to the position of the collimator into the control unit, wherein a brake on the collimator operation unit is performed based on the effective area.

7. A method for controlling a collimator configured to limit a irradiation area of X-rays generated by an X-ray generation apparatus, the method comprising:
   acquiring an effective area of a sensor based on the irradiation area of the X-rays during calibration; and
   limiting a movement range of the collimator based on the effective area.

8. A computer-readable storage medium storing a computer program for causing a computer to execute the control method according to claim 7.

9. The method according to claim 7, further comprising:
   determining whether a position of the collimator is appropriate based on information relating to the position of the collimator and the effective area; and
   issuing a warning when it is determined that the position of the collimator is not appropriate.

10. The method according to claim 7, further comprising inputting information relating a position of the collimator into the control unit, wherein a brake on the collimator is performed based on the acquired information.

* * * * *